United States Patent [19]

Baumann

[11] 4,386,037

[45] May 31, 1983

[54] SULPHONIC ACIDS OF TOLYL ETHER SULPHONES

[75] Inventor: Hans-Peter Baumann, Guntengarten, Switzerland

[73] Assignee: Sandoz Ltd., Basel, Sweden

[21] Appl. No.: 247,204

[22] Filed: Mar. 24, 1981

[30] Foreign Application Priority Data

Mar. 28, 1980 [CH] Switzerland ............ 2489/80

[51] Int. Cl.³ .................................. C07C 143/36
[52] U.S. Cl. ........................ 260/512 C; 8/589; 8/94.33
[58] Field of Search .................. 260/512 C, 512 R

[56] References Cited

U.S. PATENT DOCUMENTS

| | | | |
|---|---|---|---|
| 3,529,015 | 9/1970 | Steinhauer et al. | 260/512 C |
| 3,536,438 | 10/1970 | Baumann et al. | 8/21 |
| 3,538,151 | 11/1970 | Baumann et al. | 260/512 C |
| 3,781,169 | 12/1973 | Deubel et al. | 8/34 |
| 4,147,512 | 4/1979 | Kobayashi et al. | 8/165 |
| 4,247,293 | 1/1981 | Würmli | 8/94.24 |
| 4,273,903 | 6/1981 | Rose | 525/534 |
| 4,278,616 | 7/1981 | Wineholt et al. | 260/512 C |

FOREIGN PATENT DOCUMENTS 470365 3/1969 Switzerland.
470367 3/1969 Switzerland ............... 260/512 C
1377218 12/1974 United Kingdom.

*Primary Examiner*—Nicky Chan
*Attorney, Agent, or Firm*—Gerald D. Sharkin; Richard E. Vila; Thomas C. Doyle

[57] ABSTRACT

The present invention relates to sulphonic acids of ditolylether sulphones of formula I

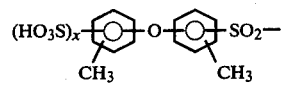

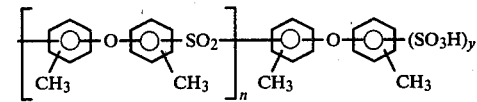

in which n is 0 to 6, each of x and y, independently, is 0 or 1 with the proviso that x+y is at least one, or salts thereof and condensates of the same with formaldehyde, which compounds are useful, inter alia, as dispersing agents for disperse dyestuff preparations.

8 Claims, No Drawings

SULPHONIC ACIDS OF TOLYL ETHER SULPHONES

The present invention relates to sulphonic acids of tolyl ether sulphones, their production and use as dyeing assistants.

More particularly, the present invention provides sulphonic acids of tolyl ether sulphones of formula I,

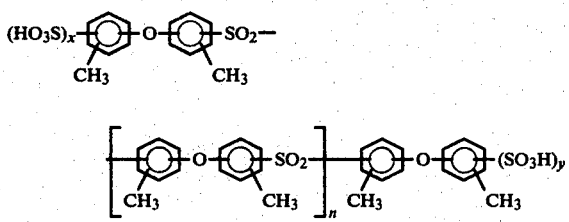

in which n is 0 to 6, each of x and y, independently, is 0 or 1 with the proviso that x+y is at least one, or salts thereof.

Preferred compounds of formula I are those which are derived from an isomeric mixture of tolyl ethers, especially those obtained as a byproduct in the preparation of cresols.

The compounds of formula I are useful as levelling agents when dyeing substrates dyeable with anionic dyestuffs or with disperse dyestuffs.

Further, the compounds of formula I are useful as dispersing agents for disperse dyes and as dispersing agents or emulsifying agents for pesticides, herbicides and other agrochemicals and as tanning assistants in the tanning of leather.

For these uses the compounds of formula I are advantageously in salt form. Suitable salt forms of the compounds of formula I include alkali metal, alkali earth metal and ammonium salts, such as sodium, lithium, magnesium, calcium, ammonium, mono-, di- and triethanolammonium and mixtures thereof.

The compounds of formula I may be prepared in analogy with known methods, for example in analogy with the methods described in Swiss Pat. No. 470,367. Basically, sulphonation is effected with 1 to 1.6 mols conc. sulphuric acid per mol tolyl ether at 110° C. and with vacuum distillation of the water of reaction, followed by condensation at 190° C. until the reaction product is water soluble and has a constant acid value. It will be appreciated that the reaction product is a mixture of compounds of different grades of sulphonation. The reaction can be illustrated as follows:

(1) Sulphonation at temperature of up to 110° C.

Tolyl-O-Tolyl + H₂SO₄ → Tolyl-O-Tolylene-SO₃H
(a) + HO₃S-Tolylene-O-Tolylene-SO₃H (b)

(2) Condensation at temperature up to 190° C. (in vacuo)

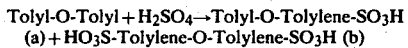
(a) $\xrightarrow{-H_2O}$ Tolylene-O—Tolylene-SO₂⁻²Tolylene-O—

Tolylene-SO₂⁻ⁿTolylene-O—Tolylene-SO₃H

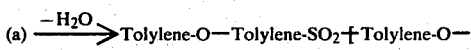
(b) + (a) $\xrightarrow{-H_2O}$ SO₃H—Tolylene-O—Tolylene-SO₂⁻²Tolylene- -continued
O—Tolylene-SO₂⁻ⁿTolylene-O—Tolylene-SO₃H The acid value of the end product is between 300 and 390 m val/100 g.

The compounds of formula I may be employed in the form of aqueous preparations or in solid form. After production the compounds of formula I need not be isolated and can be used after diluting or spray drying.

The present invention further provides a dyeing assistant composition comprising (i) a compound of formula I or a salt thereof in admixture with (ii) the condensation product of castor oil with 20 to 50 mols ethylene oxide. Suitably the ratio of (i) to (ii) is from 1.8 to 8:1, preferably from 1:2 to 2:1. This composition can also contain up to 50% by weight based on (ii) of a condensate of a fatty acid e.g. oleic acid with 5 to 10 mols ethylene oxide. This composition is particularly suitable as a levelling agent for dyeing polyamide and/or polyester fibres, especially by high temperature process.

The compounds of formula I may be employed as levelling agents either before dyeing, during dyeing or after dyeing. The pre-treatment is suitably effected at temperatures of from 20° to 100° C., preferably 50° to 100° C. in a weakly acid medium. The aftertreatment is suitably effected at 60° to 140° C., preferably from 80° to 130° C.

Dyeing and printing in the presence of compounds of formula I as levelling agents may be carried out in accordance with known methods for dyeing or printing substrates with anionic dyestuffs or disperse dyestuff. The amount of compound of formula I employed in the pre- or post-treatment bath or in the dyebath will depend on the textile substrate, the dyestuffs employed, the pH of the bath and the treatment time. In general suitable amounts are in the range of from 0.02 to 20% by weight, preferably 0.1 to 15% by weight based on the weight of the substrate.

The preferred substrates are polyesters, cellulose acetate and natural or synthetic polyamides.

The compounds of formula I have anti-foaming properties and result in level dyeings especially in the case of stripey nylon. The other properties of the dyed substrate such as light-fastness are not deteriously affected but rather improved.

When the compounds of formula I are employed as dispersing agents they are employed in accordance with known methods and in conventional amounts.

When the compound of formula I is employed as a tanning assistant it is suitably employed in amounts of from 5 to 20% by weight based on the tanning agent (solids), preferably about 10% by weight.

The compounds of formula I can also be reacted with from 0.2 to 3 mols formaldehyde, a formaldehyde yielding agent or methylol compound/mol compound of formula I in the presence of strong sulphuric acid (pH below 1). The products are also useful as dispersing agents for disperse dyestuffs.

The following Examples further serve to illustrate the invention. In the Examples all parts are by weight and all temperatures in degrees Centigrade.

EXAMPLE 1

588 Parts sulphuric acid (98%) are added under nitrogen atmosphere with vigorous stirring and cooling to 792 parts tolyl ether over a period of 30 to 45 minutes. After addition the temperature is between 100° and 105°. The reaction is continued for 5½ to 6 hours. With a vacuum (10–15 torr) the temperature is raised to 120° in 10 to 20 minutes. After 20 to 30 minutes the water of the reaction is practically fully removed. Reducing the vacuum to 3 to 6 torr the reaction mixture is heated for approximately 15 minutes to a temperature between 160° and 180° and the whole is kept at this temperature for about 6 hours until the acid resin produced has an acid content of 330 to 390 m val/100 g. The reaction mixture is cooled (without vacuum) in 10 to 15 minutes, to 125° to 130°. The product, without isolation, is then further treated with 500 parts demineralised water at a temperature of 8°–12°. (The nitrogen atmosphere can be removed). The aqueous solution of the resin is cooled to 90° to 100° and 355 parts of aqueous ammonia (25%) are added slowly thereto over a period of 30 minutes with cooling. After the addition the temperature of the solution is 30° to 35°. Stirring is effected for about 30 minutes at 20° to 30° until a fully homogeneous solution is obtained. The weak viscous solution has a pH in the range of 6.5 to 7. The solution may then be diluted with 270 parts water and stored used as such or it can be converted to a powder by spray drying.

EXAMPLE 2

A 50% aqueous solution of the product of Example 1 (50% active material) in the ammonium salt form is mixed with 16% by weight based on the active material of condensate of castor oil with 32 mols ethylene oxide. The viscous solution is stable on storage.

EXAMPLE 3

40 Parts anhydrous product of Example 1 (in acid free form) are stirred with 60 parts condensate of castor oil with 32 mols ethylene oxide at 100° until homogenity is obtained. Subsequently 12 parts monoethanolamine are added with cooling. When 50 parts are added a viscous storage-stable product is obtained.

EXAMPLE 4

A similar product to that of Example 3 is obtained by mixing 10, 90, 3 and 15 parts of the given ingredients in place of the 40, 60, 12 and 50 parts, respectively.

EXAMPLE 5

15 Parts anhydrous product of Example 1 are neutralized with 5 parts monoethanolamine. 12 parts paraffin oil, 4 parts condensate of oleic acid with 6 mol ethylene oxide, 60 parts condensate of castor oil with 32 parts ethylene oxide and 4 parts water are added and stirred until homogenity is obtained. The product is especially suitable as a levelling agent for the high temperature dyeing of polyester.

EXAMPLE 6

10 Parts anhydrous product of Example 1 and 47 parts ethanol are neutralized with 3 parts monoethanolamine. Then 40 parts of carrier consisting basically of trimethylbenzenes as described in DOS 2 033 894 in the Table under 3, column 6 are added and the whole is stirred under homogenous. A clear yellow solution with good levelling properties for dyeing polyester by the high temperature process is obtained. Similar results are obtained employing instead of 40 parts trimethylbenzene, 40 parts ditolylether.

EXAMPLE 7

100 Parts stripey nylon are dyed in a dyebath (liquor to goods ratio 40:1) containing 0.35 parts dye of formula

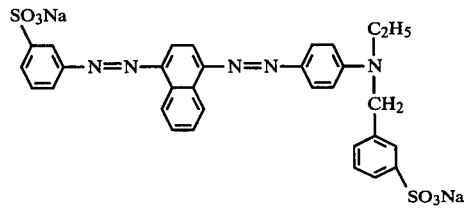

3 parts $NaH_2PO_4$ and 6 parts compound of Example 1 (100% active ingredients-ammonium salt). The bath pH is 6 and the fabric is put into the bath at 50° whereupon the bath is heated to 98°–100° in 45 minutes and dyeing is carried out at this temperature for 60 minutes. The substrate is then rinsed and dried. A level, stripe-free red brown dyeing is obtained.

EXAMPLE 8

A yarn consisting of 50 parts nylon 6.6 and 50 parts Spandex fibres (Lycra, Dupont) are dyed in a bath (liquor to goods ratio 40:1) containing 0.25 parts sodium salt of 1-amino-2-bromo-4-(4'-methylphenylamino)-anthraquinone-2'-sulphonate, 2 parts acetic acid and 2 parts of the ammonium salt of the compound of Example 1 (100% active substance). The yarn is added to the bath at 35° and the bath is heated to 95° in 40 minutes. Dyeing is effected for 1 hour at this temperature. Both yarns are equally dyed in the same tone of blue. With 4 parts of the composition of Example 2 equally good results are obtained.

EXAMPLE 9

A bobbin of polyester texturised yarn is dyed at a liquor to goods ratio of 10:1 in a bath at 130° containing demineralised water (pH 4.5 adjusted with acetic acid) 1 g/l compound of Example 1 in the $NH_4$ salt form 100% active material) and 1 g/l of the condensate of castor oil with 30 mols ethylene 0.46% dyestuff of formula I

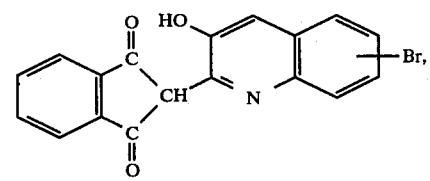

0.52% dyestuff of formula II

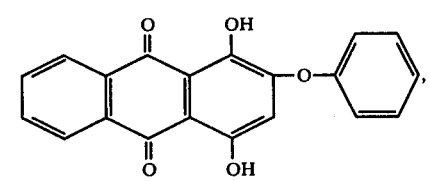

0.17% dyestuff mixture of equally quantities of dyes of formulae III and IV

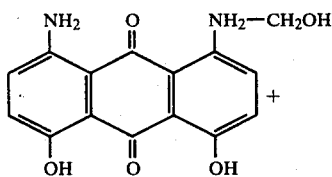

III

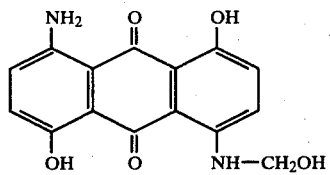

IV

The amount of liquid flowing was equivalent of 20 l/kg per minute. After 30 minutes treatment at 130° the whole is cooled, the bath is run off and the substrate is subjected to reductive clearance. Equally good results are obtained employing 2 g/l of the composition of Example 2.

EXAMPLE 10

A polyester fabric (Dacron) is dyed with 0.25 g/l Foron Rubin SE-GEL with the addition of 2 g/l ammonium sulphate and 2 g/l compound of Example 1 ($NH_4$ salt 100% active substance) at pH 5. The liquor to goods ratio is 20:1. The dyeing is begun at 20° and the bath is heated to 70° in 10 minutes. The dyeing is completed after 20 minutes at 130°. A level dyeing is obtained. Using the same amount of the compounds of Examples 2 to 5 equally good results are obtained.

EXAMPLE 11

214 Parts of C.I. Disperse Blue 73 (pure dyestuff) in the form of a presscake are stirred well with 1050 parts of solution of the compound of Example 1 (389 parts active substance for 16 hours until a lump-free suspension is obtained. The suspension is put through a sieve then homogenised for 2 hours in a homogenising machine until the majority of the particles are 1μ or less. The homogenate is spray-dried and 603 parts of a dyestuff powder having good dispersion stability are obtained. The dyestuff powder also gives good dye yield on textile substrates.

EXAMPLE 12

A storage (stable 60% tanning liquid is made from
8 parts $Cr_2(SO_4)_3$ (powder)
4 parts ammonium salt of Example 1 (100% active ingredients.
0.5 parts formic acid and
7.5 parts water.

Using this tanning liquid, leather of good quality is obtained employing the chrome-tanning process. [Zirconium sulphate in place of chromium sulphate gives equally good results].

EXAMPLE 13

80 Parts herbicide N-(3,4-dichlorophenyl)-N'N'-dimethyl urea is ground with 5 parts compound of Example 1 ($NH_4$ salt 100% active material) 1.25 parts dibutylnaphthalenesulphonate 4 parts silica gel and 9.5 parts aluminia.

In a 1% dispersion in water having 5° German Hardness less than 25% of the agent is precipitated.

EXAMPLE 14

3 Parts C.I. Disperse Blue 71 powder are stirred to homogenity with 10 parts of a 30% aqueous solution of the compound of formula I, then ground in a mill having glass beads of 0.4 to 0.6 mm for 50 minutes. The suspension obtained has good storability and is easy to use.

EXAMPLE 15

To 680 Parts ditolylether (isomeric mixture of dimethyldiphenylether) are added dropwise under nitrogen atmosphere, 588 parts (concentration 98%) sulphuric acid over 40 minutes at 108°.

After stirring the reaction mixture for 6 hours at 100° the temperature is raised to 120° under vacuum (15 torr). Condensation is effected at this temperature for 1 hour. Subsequently the whole is heated to 160° under increased vacuum (0.1 to 1.1 torr). After a further 6 hours at 160°, 1051 parts of a sulphone with an acid value of 381 m val/100 g is obtained. 86.8 parts sulphone and 20 parts water are warmed to 100°. After the solution is homogeneous, 6.3 parts formaldehyde (35.8%) and 2 parts (vol.) sulphuric acid (concentration 98%) are added. Condensation is effected for 14 hours at 102°. The viscous brown solution obtained is neutralized with ammonium hydroxide and dried on a rotary evaporator or in vacuo. The product is a light brown powder which is easily soluble in water. Neutralization with an equivalent amount of $NH_4OH/Mg(OH)_2$ yields, after spray drying, a light grey-brown powder which is well soluble in water is obtained.

What is claimed is:

1. A compound of formula I,

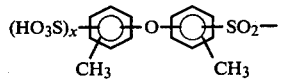

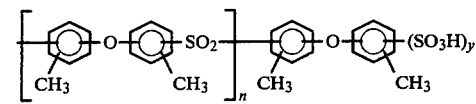

in which n is 0 to 6, each of x and y, independently, is 0 or 1 with the proviso that x+y is at least one, a salt thereof.

2. A compound according to claim 1 which in salt form is an alkali metal, alkali earth metal or ammonium salt.

3. A compound according to claim 2 which in salt form is a sodium, lithium, magnesium, calcium, ammonium or mono-, di- or triethanol ammonium salt.

4. A compound according to claim 1 prepared from an isomeric mixture of tolyl ethers.

5. A compound according to claim 1 having an acid value between 300 and 390 m val/100 g.

6. The condensate of a compound of formula I as defined in claim 1 with 0.2 to 3 mols formaldehyde, formaldehyde yielding agent or methylol compound per mol of compound of formula I.

7. A condensate according to claim 6 derived from a compound of formula I prepared from an isomeric mixture of tolyl ethers.

8. A condensate according to claim 6 derived from a compound of formula I having an acid value of 300 to 390 m val/100 g.

* * * * *